United States Patent [19]

Marinoff

[11] 4,340,059
[45] Jul. 20, 1982

[54] RADIAL KERATOTOMY DEVICE

[76] Inventor: Gerald P. Marinoff, 8 Rockford Dr., West Nyack, N.Y. 10994

[21] Appl. No.: 199,693

[22] Filed: Oct. 23, 1980

[51] Int. Cl.³ ............................................. A61B 17/32
[52] U.S. Cl. .................................................. 128/305
[58] Field of Search ..................... 128/305, 305.1, 310; 33/19 B, 21 R, 21 B, 174 D

[56] References Cited

U.S. PATENT DOCUMENTS

| | | | |
|---|---|---|---|
| 2,249,906 | 7/1941 | Longoria | 128/305 |
| 2,480,737 | 8/1949 | Jayle | 128/305 |
| 2,932,296 | 4/1960 | Sanders | 128/305 |
| 4,180,075 | 12/1979 | Marinoff | 128/305 |

OTHER PUBLICATIONS

"Shaping up the Blurry Eye", Time Magazine, Sep. 22, 1980, p. 51.
Proceedings of the Keratorefractive Society, pp. 141–244, (Jun. 21, 1980).

Primary Examiner—Michael H. Thaler
Attorney, Agent, or Firm—Arthur Dresner

[57] ABSTRACT

A hand-held surgical instrument for performing ophthalmological incisions in the form of radial slits about the cornea, which are particularly suited for surgery to correct the effects of myopia or astigmatism. The instrument includes a fixation assembly having a pair of elongated arms for placement on the globe of the eye. A prong is carried at one end of each arm for insertion into the globe of the eye so that the surgeon may hold the eye in a fixed position. A linkage assembly is connected at one end to the fixation assembly and a knife assembly is connected to the other end of the linkage assembly for indexing movement about a pivot point. The knife assembly includes a knife blade holder and a knife blade carried in the holder. The blade holder is mounted for sliding movement toward and away from the pivot point so that the cutting edge of the blade will penetrate the eye to form radial slits upon the application of sufficient hand pressure.

18 Claims, 9 Drawing Figures

FIG. 1
FIG. 2
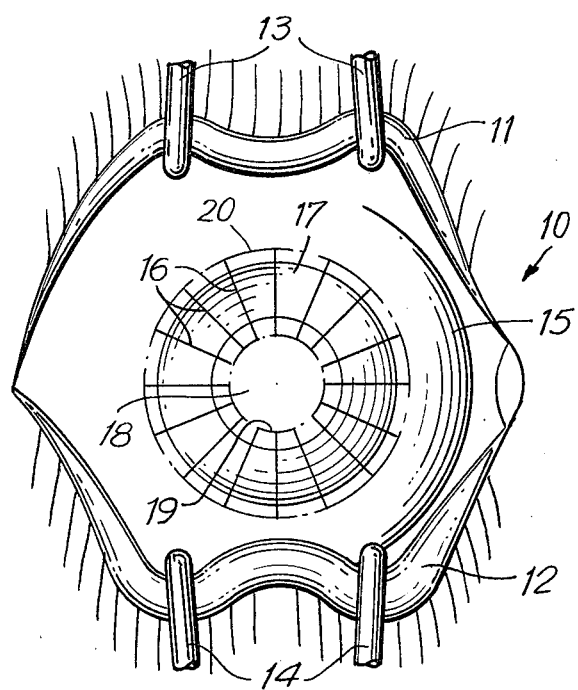
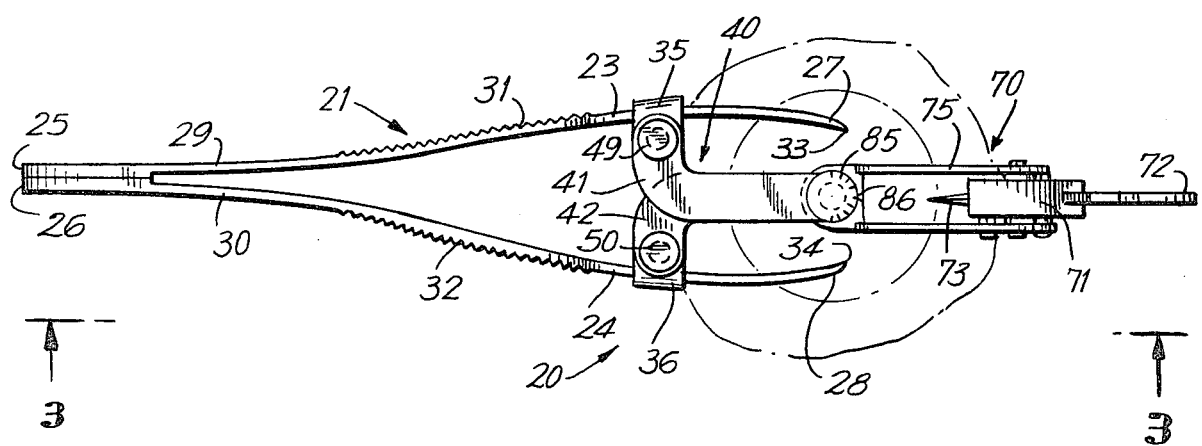

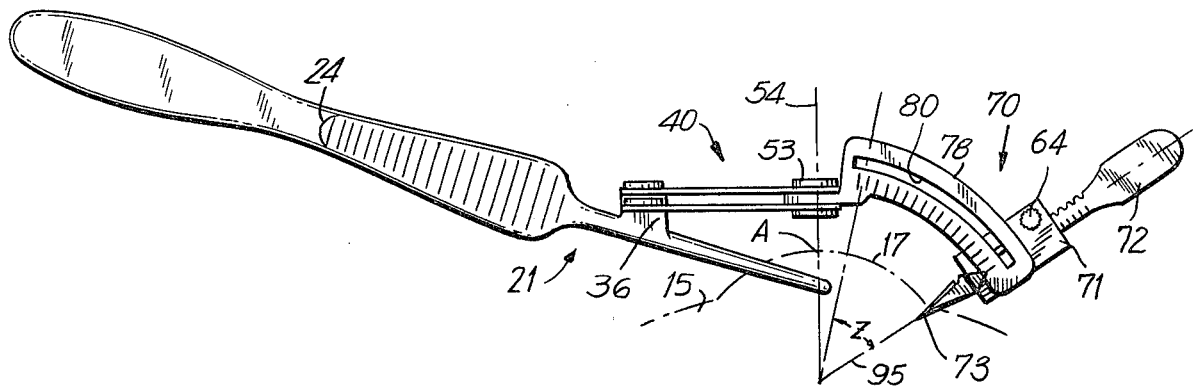
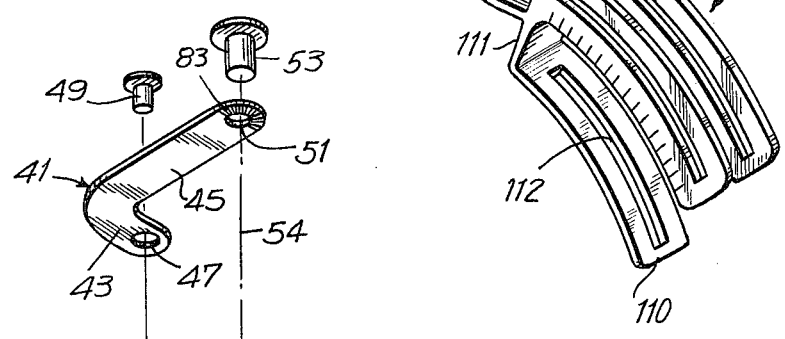
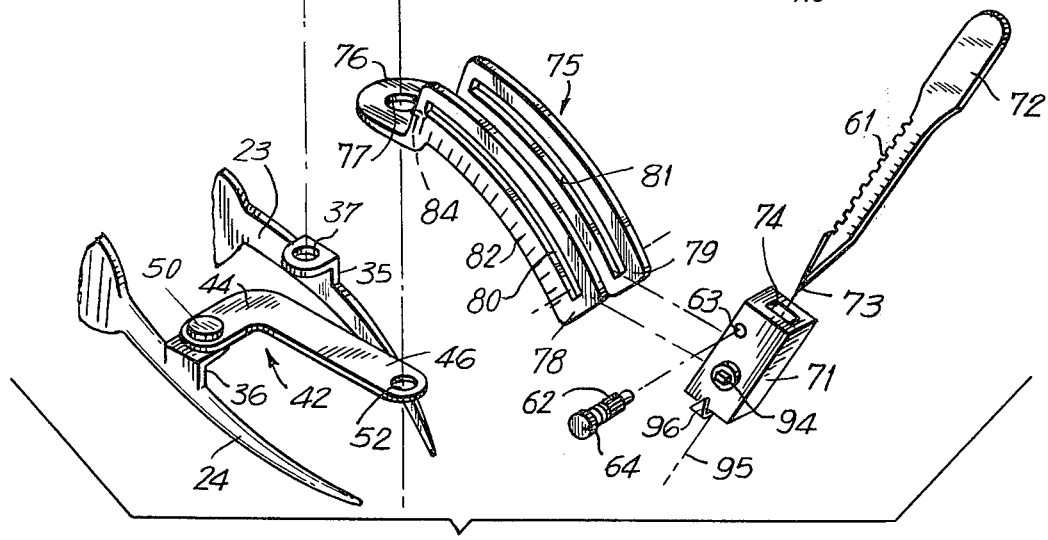

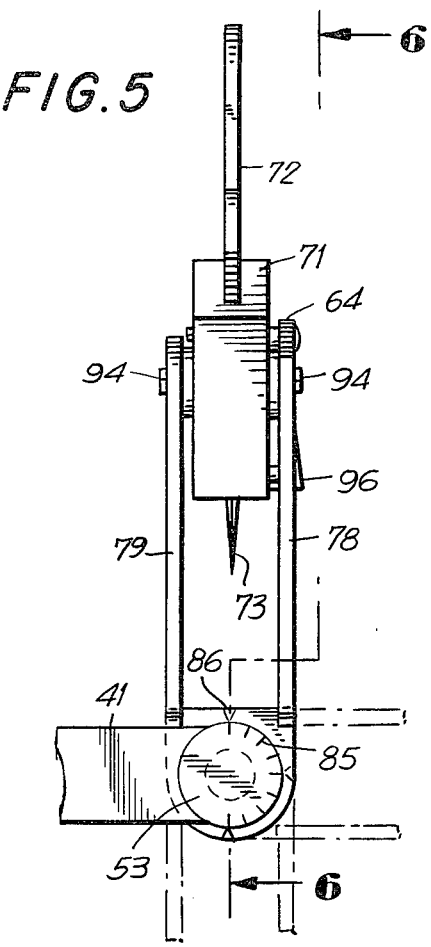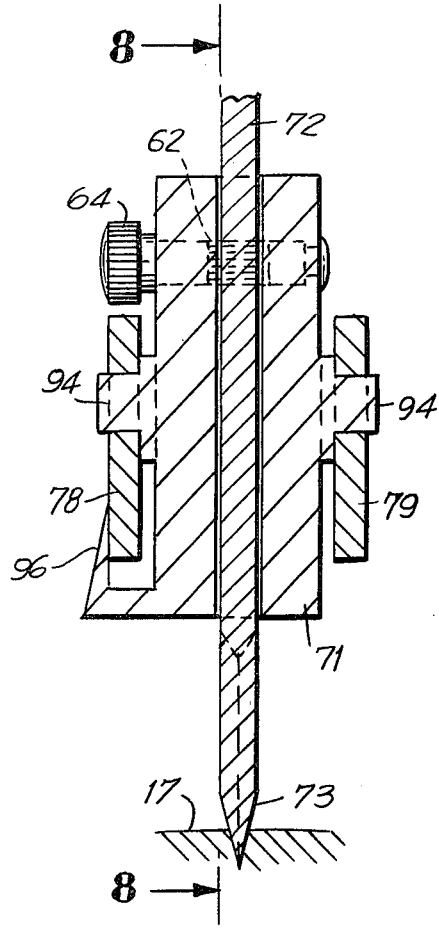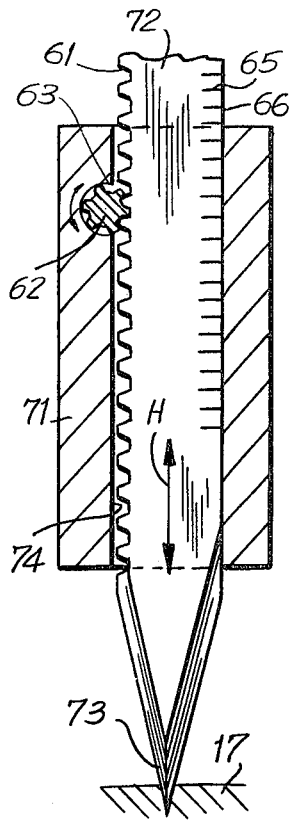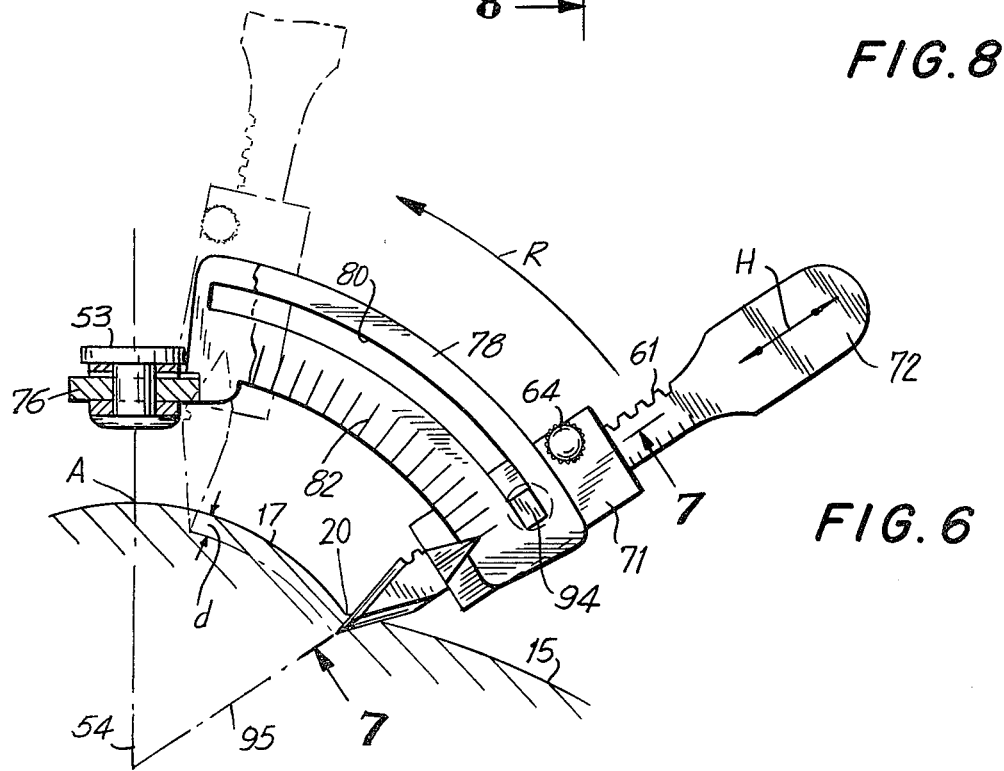

RADIAL KERATOTOMY DEVICE

BACKGROUND OF THE INVENTION

The invention relates generally to the field of surgical instruments and is more particularly directed to a hand-held surgical instrument used for forming radially oriented incisions particularly suited for surgery to correct the effects of myopia or astigmatism.

It has been determined that myopia (or nearsightedness) and astigmatism are directly related to the curvature of the eye, and in particular of the cornea. Varying the degree of curvature of the cornea will, therefore, directly affect the degree of myopia and astigmatism. Recently, surgical techniques have been developed to vary the degree of curvature of the cornea. These techniques involve the placement of radial incisions, varying in length, about the cornea and extending up to or into the sclera. Further descriptions of this surgical technique can be found in articles by Professor S. Fyodrov; William D. Myers, M.D.; Leo Bores, M.D.: Ronald A. Schacher, M.D., et al; Ronald A. Schacher, M.D. alone; and Ronald A. Schacher, M.D. with Les Schacher, M.D.; all published in the Proceedings of the Keratorefractive Society for the meeting dated June 21, 1980.

Heretofore, the placement of the radially arranged incisions has been accomplished by free hand. Placement and positioning of the incisions has thus far, been the result of the surgeons eye judgement. The success or failure of the technique to vary the curvature of the cornea will depend to a great degree on the proper spacing of the radial incisions. It is desirable that the incisions be equi-distantly spaced to enhance the control of the procedure.

It has also been found that the depth of the incisions is a critical factor in determining the degree of varying the curvature of the cornea.

The length of the incisions, the remaining optical zone and the angle of the incisions with respect to the surface of the cornea are also critical factors in performing a successful procedure. It has been found desirable that the angle of the incisions be 90° (i.e. perpendicular) with respect to the surface of the cornea. Incisions which are not perfectly radial will also have an adverse effect on the results of such an operation.

Because the radial incisions have heretofore been typically formed by free hand, no two operations can ever be expected to be exactly the same. Further, control over the critical factors (i.e. spacing, length, depth and perpendicularity) are difficult, if not impossible, to control when forming the incisions by free hand. The results to be expected from such surgical procedures cannot, therefore, be predicted when using a free hand technique.

It is, accordingly, a general object of the present invention to provide an ophthalmological surgical instrument, useful for forming perfect radial incisions about the cornea which overcomes the disadvantages of using a free hand technique.

It is a more specific object of the present invention to provide such a surgical instrument which enables the surgeon to accurately space the radial incisions equi-distantly for uniformity and predictable results.

It is yet a further object of the present invention to provide a device for forming radial incisions in the cornea of the eye which has means for adjusting and controlling both the spacing of the radial incisions and the depth of the incision.

Another object of the invention is to provide a radial keratotomy device having means to control the length of the radial incisions and therefore, the size of the optical zone.

Still a further object of this invention is to provide a device for forming radial incisions in the cornea which are perpendicular to the surface of the cornea.

The above objects, features and advantages, along with other objects, features and advantages of the present invention will become more apparent from the detailed description of the invention in conjunction with the accompanying drawings to be described more fully hereinafter.

SUMMARY OF THE INVENTION

The present invention is directed to a hand-held surgical instrument to facilitate making radial incisions required during surgical techniques to correct myopia and astigmatism.

The instrument of the present invention includes a fixation assembly having a pair of elongated arms. A prong is carried at one end of each arm for insertion into the globe of the eye so that the surgeon may hold the eye in a fixed position. A linkage assembly is connected at one end to the fixation assembly and a knife assembly is connected to the other end of the linkage assembly for indexing movement about a pivot point. The knife assembly includes a knife blade holder and a knife blade carried in the holder. The blade holder is mounted for sliding movement along a curved path toward and away from the pivot point so that the cutting edge of the blade will penetrate the eye to form radial slits upon the application of sufficient hand pressure.

The foregoing and other features of the present invention are more fully described with reference to the following drawings annexed hereto.

BRIEF DESCRIPTION OF THE DRAWINGS

FIG. 1 is a plan view of the globe of the eye with eyelids shown in a retracted position and showing an example for locating the radial incisions to be performed with the present invention;

FIG. 2 is a plan view showing the invention when positioned for use on the globe of a patient's eye to perform the radial incisions;

FIG. 3 is a side elevational view of the invention shown in the same position for operative use;

FIG. 4 is a partial exploded view showing the relationship of various elements of the invention;

FIG. 4(a) is a perspective view of an alternative embodiment of one of the elements of the invention;

FIG. 5 is a partial enlarged plan view of the invention;

FIG. 6 is a sectional elevational view taken along lines 6—6 of FIG. 5;

FIG. 7 is a sectional view taken along lines 7—7 of FIG. 6; and

FIG. 8 is a sectional view taken along lines 8—8 of FIG. 7.

DESCRIPTION OF THE INVENTION

Referring now in greater detail to the accompanying drawings, FIG. 1 shows in plan view a representation of a human eye as prepared for surgery to correct myopia or astigmatism. The eye, indicated generally by reference numeral 10, has upper and lower eyelids 11 and 12, respectively, which are held in a retracted position by a pair of commonly used lid retractors 13, 14. These are commercially available, such as from the Storz Instrument Company under Catalong Nos. E-996, E-997, E-998 or E-1000. Retraction of the eyelids reveals a major portion of the globe 15 of the human eye so as to provide sufficient room for the surgeon to prepare the eye for the surgical procedure.

The particular placement, length and depth of the radial incisions will depend upon a number of objectives of the surgeon. However, placement of these incisions by free hand will rarely result in uniform results as to position length, radiality, perpendicularity or depth. As hereinbefore noted, it is therefore the principle object of the present invention to enable the surgeon to perform precise radial incisions for which the length, depth, perpendicularity and position can be accurately controlled.

For purposes of explanation and understanding the present invention, and with reference to FIG. 1, the device of the present invention is intended for placement of a plurality of radial incisions 16 about the cornea 17. It has been found, and FIG. 1 illustrates, that sixteen incisions equi-distantly spaced about the cornea usually produces satisfactory results. More or less, incisions may be placed depending upon the seriousness of the patient's condition, and the degree of correction desired. An optical zone 18 is established by the surgeon and might be delineated by a slight score mark 19. The size of the optical zone 18 will depend on the refractive era, but will generally range from about 2.5–5.0 millimeters. The posterior border of the limbus is indicated generally by reference numeral 20. The length of the incisions 16 will depend upon the results to be achieved. However, incisions ranging in length from about $\frac{1}{2}$ millimeter to about 6.0 millimeters, and preferably about 4.0 millimeters, have been found to be acceptable. Such incisions, if performed free hand, would require an unusually steady hand. It is likely to expect that free hand incisions would not be exactly positioned radially about the cornea, but might extend along a chord. Additionally, the angle of the incision, with respect to the surface of the cornea, might not be precisely perpendicular. It has been found that perpendicular incisions are preferable to those forming an acute angle with the surface of the cornea. The use of the present invention, however, makes the formation of these incisions a relatively simple matter regardless of the skill of the surgeon. The critical elements of length, radial placement, depth and perpendicularity with the surface of the cornea can be precisely controlled as will be appreciated hereinafter.

In order to perform the incisions of the radial keratotomy, the retractor 13 is positioned on the upper eyelid (the one toward the patient's forehead), while the retractor 14 is positioned at the patient's lower eyelid (the one adjacent the patient's cheek). After the incisions 16 are placed, using the present invention, the cornea 17 will have been flattened, thus correcting the myopia or astigmatism.

The device of the present invention, which will be used in order to perform the operation described in connection with FIG. 1, is illustrated in FIGS. 2 through 8.

Referring now in more detail to FIGS. 2 through 8, the keratotomy device 20 of the present invention includes three basic elements or substructures. The first element 21 is a fixation device and is used as a means by which the surgeon will engage the globe of the human eye in order to fix its position while the incisions are being formed. This is a significant element of the present invention in that it enables the surgeon to either prevent movement of the globe of the eye while performing the incisions, or to grasp and rotate the eye as desired. It also provides a means for establishing a fixed point of reference for positioning the cutting blade, to be described more fully hereinafter.

One type of fixation device found to be satisfactory for the purposes of the present invention is a device similar to a commonly used forceps, a tong-like device for delicately but firmly holding the eye. The fixation device intended for use in the present invention comprises a pair of arms 23 and 24, each of which are preferably made of spring steel. Each of the arms 23 and 24 are fixed to each other at 25 and 26, respectively, while the opposite or distal ends 27 and 28, respectively, are free to move toward and away from each other. The upper shank portions 29 and 30 of each of the arms may be pre-stressed so that movement of the arms toward or away from each other will result in return of the arms to an original position. Each of the arms is also provided with a finger grip area 31 and 32 having a roughened or non-slip surface so that the surgeon will be able to hold the fixation device between his fingers without fear of it slipping. The free or movable ends 27, 28 carry prongs 33, 34 each of which may be approximately 2 mm long. When the fixation device is used by the surgeon, the prongs will be forced to partially penetrate the sclera of the globe of the eye so that the surgeon will have a firm grip to fix the position of the globe and prevent rotation or movement during the incision procedure. Shoulders 35 and 36 are carried by arms 23 and 24 to provide a point of connection and support for the linkage assembly 40, to be described in greater detail below.

A knife assembly 70 forms the second basic element of the invention and includes a knife blade holder 71 and the knife itself 72 carried in a channel 74. The knife may be of the commercially available type, such as the commonly used Beaver Knives sold by the Storz Instrument Company and modified as described below.

This knife has a cutting edge 73 for penetration of the cornea. Means, to be described more fully hereinafter, are provided to vary and control the exposure of the cutting edge 73 so as to adjust the depth to which the cutting edge will penetrate the eye. The knife assembly also includes a linkage arm 75 to support the holder 71 for movement therealong.

The third basic element of the present invention is the linkage assembly, referred to generally as reference numeral 40. This element serves to link the knife assembly 70 with fixation device 21 in order to provide a fixed relationship therebetween and to provide means for accurately indexing the knife assembly to the various positions for the incisions.

The linkage assembly 40 includes first and second "L" shaped arms 41 and 42, each having short legs 43, 44 and long legs 45, 46, respectively. Each of the short legs 43, 44 is pivotally connected to one of the arms of the fixation assembly 21. For this purpose, arms 23 and 24 carry the shoulders 35 and 36, respectively. Each shoulder is provided with a hole 37. The distal ends of the legs 43 and 44 are also provided with holes 47 and 48. As will be fully appreciated from the exploded view of FIG. 4, "L" shaped arms 41 and 42 are mounted on the movable arms 23 and 24 of the fixation assembly by rivets 49 and 50 which extend through the holes 47 and 48 of each of the "L" shaped arms and the corresponding holes 37 of the shoulders 35 or 36.

Apertures 51 and 52 are located at the distal end of long legs 45, 46, respectively. Apertures 51 and 52 are aligned with each other when the "L" shaped arms 41, 42 respectively, are connected to the fixation assembly 21. A pivot pin or rivet 53 extends through apertures 51 and 52 to form a pivot point defined by pivot axis 54. When rivets 49 and 50 are in place to secure the short legs of the "L" shaped arms to the fixation assembly, and when pivot pin 53 is in place to secure the long legs of the "L" shaped arms, movement of arms 23 and 24 toward and away from each other will result in a scissor like movement of the "L" shaped arms 23, 24 with respect to each other.

Linkage arm 75, which forms part of the knife assembly 70, has a flange 76 with an aperture 77 so that it may be connected to the "L" shaped arms 41 and 42 by rivet 53 passing through the aperturs 51, 52 and 77 so as to join all three links together at a common pivot point defined by the pivot axis 54.

Linkage arm 75 has a pair of spaced apart parallel extending side walls 78 and 79. Walls 78, 79 have guide slots 80, 81 respectively. Slots 80 and 81 extend along a curved path. The path is intended to be approximately concentric with the normal curvature of the cornea for reasons to be described more fully hereinafter. On the outside of wall 78 is a scale 82 graduated in millimeters for purposes to be described more fully hereinafter.

The under surface of "L" shaped arm 41 is provided with a plurality of radially oriented indentations 83 spaced about aperture 51. For the purposes of the present embodiment, eight such indentations are arranged equi-distantly through 180° about aperture 51. A detent member 84 is carried on flange 76 of link 75 for mating engagement with one of the indentations 83. Accordingly, when link 75 is pivoted about the pivot axis 54, extending through rivet 53, positive engagement between the detent 84 and one of the indentations 83 will cause link 75 to move incrementally about the pivot point. Incremental indexing of the link 75 about the pivot point through eight equally spaced positions is, therefore, made possible.

In order for the surgeon to determine the particular position of the link 75 about the pivot point, the top surface of rivet 53 may be provided with a scale 85. A pointer 86 is provided on flange 76 so that as the link 75 is incrementally indexed about the pivot axis 54, the surgeon will be able to determine the degree of indexing and the particular radial position of the link 75.

Knife blade holder 71 has a pair of square shaped trunnions 94. When assembled with link 75, the knife blade holder 71 will fit between walls 78 and 79 with trunnions 94 positioned within the guide slots 80, 81. The flat surface of the trunnions 94 are oriented so that when the knife blade 72 is carried within the channel 74, the longitudinal axis 95 of the knife blade 72 will lie along a line substantially coincident with a radial line extending from the center of the cornea. The trunnions are dimensioned so that the blade holder 71 can be freely moved along the curved path formed by slots 80, 81.

A pointer 96 is carried on the bottom of the blade holder 71. When the holder 71 is positioned between walls 78 and 79, the pointer 96 will be aligned with the scale 82 on side wall 78. Accordingly, the surgeon will be able to determine the exact amount of movement of the blade holder 71 along the slots 80, 81 and therefore, the exact length of the incisions 16 can be controlled.

In order to accurately adjust the depth of cut, the amount of exposure of the cutting blade 73 is adjustable. For this purpose, knife blade 72 carries a rack 61 along one side thereof. A pinion 62 is rotatably carried within an aperture 63 extending through the knife blade holder 71 for engagement with the rack 61. Aperture 63 communicates with the blade holding channel 74. An adjustment knob 64 is connected to the pinion 62 so that external adjustment of the knife blade within the knife blade holder in the direction of arrow H (see FIG. 8) is possible. Knife blade 72 is provided with a scale 65 along the edge 66 opposite the edge having rack 61. Accordingly, as the knife blade 72 is adjusted upward or downward (i.e., in the direction of arrow H), the scale 65 will be viewed by the surgeon to determine the degree of exposure of the cutting edge 73.

When the "L" shaped arms 41, 42 are connected to the fixation device, as described above, the linkage arm 75 will be connected, at its flange end, to the distal ends of the long legs 45, 46 of the "L" shaped arms, and the knife assembly will be linked to the fixation device so that the knife may be moved by one hand of the surgeon along the slots 80, 81 to form the incisions.

In operation, using the fingers of one hand, the surgeon will first grip the fixation device moving the arms 23 and 24 apart where necessary so that the prongs 33, 34 may be placed on the desired position of the globe of the eye. The surgeon will then apply sufficient pressure to the arms 23, 24 so that they will be moved toward each other and so that the prongs 33, 34 will pierce the sclera and penetrate to a depth sufficient for the surgeon to maintain the fixation device in place with little additional pressure, thus fixing the globe of the eye of the patient. In moving the arms 23, 24 toward and away from each other, the "L" shaped arms 41, 42 will move in a scissor like manner, being joined at the pivot point defined by the rivet 53. Once the fixation device is in place, no further movement of the arms 41, 42 will take place.

It will be seen from FIG. 3 that in placing the fixation device in the desired position, the pivot axis 54 will preferably pass through the center of the cornea (a point indicated by the reference letter A). After the fixation device is in position, in order to bring the cutting edge 73 of the blade 72 into contact with the eye, the surgeon will rotate or pivot the fixation device about the point where the prongs have penetrated the globe until the curved slots 80, 81 lie on a path approximately concentric with the curvature of the cornea. At this point, the knife blade 73 will penetrate the eye to the desired depth as determined by the preset longitudinal position of the blade 72 within the channel 74 as a result of having rotated the knob 64. With the fingers of the other hand, the surgeon will then grip the knife assembly, either by holding the upper end of the knife blade holder 71, or the upper end of the knife blade 72, causing it to move in a radial direction, i.e. arrow R (FIG. 6).

Initial placement of the cutting edge will be at the surgeons discretion and may be at the boarder of the optical zone, or at the outer extent of the incision near or at the limbus 20, as illustrated in FIG. 2. The surgeon can easily control the length of incision by noting the position of the pointer 96 with respect to the scale 82. Movement of the blade through the cutting angel Z (FIG. 3) will determine the length of the incision. Moving from one end of the slots 80, 81 to the other will result in the maximum length of incision.

The depth d, which will range from 0.3 mm to 0.9 mm (see FIG. 6), can also be varied by adjustment of knob 64, preferably to an accuracy of 0.005 mm.

After the first incision 16 (about to be started at the 3 o'clock position, as seen in FIG. 3) is formed, the fixation device can be pivoted about the prongs 33 and 34 so that the knife blade 73 will lift off the surface of the eye. The surgeon may then index the knife assembly 70 about the pivot point defined by axis 54 to the next desired position. The cutting edge 73 will once again be placed on the surface of the eye. The blade 72 will again be moved in a radial direction to form a second incision at the desired location. This process will be continued until it is necessary for the surgeon to lift the fixation assembly from the surface of the eye and reposition it for continuing the placement of incisions until all incisions are formed.

An alternative construction for link 75 is illustrated in FIG. 4(a). In this embodiment, the link 75' is provided with a guide plate 110 which may be supported from the flange 76' by a downwardly extending support member 111. Plate 110 is curved to coincide with the radius of curvature of the cornea. When the instrument of the present invention is placed in use and the fixation device is pivoted about the prongs so that the knife blade will penetrate the eye, the plate 110 will come to rest on the surface of the cornea conforming to its shape. A guide slot 112 is formed in the plate 110 through which the cutting edge 73 of the blade will extend. The plate 110 thereby serves as a further guide or template for positioning the cutting edge 73.

Any other suitable means for supporting the knife blade holder 71 so that the cutting edge 73 will extend through and be guided by the guide slot 112 of the plate 110 may be equally satisfactory as an alternative to the use of walls 78 and 79 with guide slots 80 and 81 for receiving the trunnions 94. In such case, the plate 110 may be provided with a scale along one edge thereof so that a pointer on the knife blade holder will indicate the length of the incision.

The use of the plate 110 further serves to limit the depth of insertion of the knife blade cutting edge 73.

FIG. 5 illustrates the position of link 75 in solid lines for making an incision along a radial line through the 12 o'clock position. At this position, the axis of link 75 is oriented at an angle of 90° with respect to the axis of link 41. Pointer 86 indicates this condition by alignment with one of the extreme markings on the scale 85 on rivet 53. Link 75 can then be indexed in a clockwise direction through eight separate positions from 12 o'clock to 6 o'clock. Scale 85 on the head of rivet 53 will indicate each of the positions. Link 75 is shown in phantom lines at the 3 o'clock and 6 o'clock positions.

Precise positioning of link 75 at each of the eight positions is accurately controlled by the indentations 83 equally spaced about aperture 51 on the bottom of link 41 and the cooperating detent 84 on flange 76 of link 75. More or less discrete indexing positions can be provided by changing the numer and spacing the indentations. Thus, indexing to each of the discrete positions for equal spacing of the incisions is insured.

After the first eight incisions (from 12 o'clock to 6 o'clock) are placed, it will be necessary for the surgeon to reposition the fixation device so that the next eight incisions from the 6 o'clock to the 12 o'clock positions can be made.

In order to insure that the incisions will be in the desired area, the dimensions of the various links will be designed such that when the pivot point through axis 54 is placed in substantial alignment with the center of the cornea A, the knife blade 73 will penetrate at the desired location. Since the dimensions of all human eyes, and the various elements thereof, are substantially identical, the cornea being substantially circular with a radius of about 6 mm, proper dimensioning is a simple matter.

The present invention allows the surgeon to describe radial incisions with complete accuracy and uniformity because of the fixed relationship between the position of the blade and the center of the cornea as determined by the dimensions of the linkage assembly, and because of the indentations 69 and detent 68 arrangement for positive indexing. Additionally, the present invention allows the surgeon the greatest degree of flexibility in positioning the knife cutting edge in the proper area and maintaining the most comfortable position of the fixation device.

While the invention has been described and illustrated with respect to certain embodiments which produce satisfactory results, it will be understood by those skilled in the art, after understanding the purposes of the invention that various other changes and modifications may be made without departing from the spirit and scope of the invention, and it is, therefore, intended in the appended Claims to cover all such changes and modifications.

What is claimed is:

1. A hand-held surgical instrument for performing radial ophthalmological incisions comprising fixation means for supporting said instrument on the globe of an eye and adapted to be held in one hand of a surgeon; a linkage assembly connected to said fixation means; a knife assembly connected to said linkage assembly including a knife blade holder and a knife blade removably carried therein for forming incisions in the eye of a patient; said knife assembly including a linkage arm pivotally connected to said linkage assembly at a pivot point for indexing movement thereabout; said linkage arm carrying a pair of spaced guide walls extending away from said pivot point, guide means formed in each of said walls along a curved path, support means carried by said knife blade holder and positioned to cooperate with said guide means in said walls to prevent swinging movement of said knife blade thereby supporting said knife blade holder between said walls for movement along a path toward and away from said pivot point, whereby when said surgical instrument is in an operative position and said blade is moved along said path, said blade will penetrate the eye to form an incision radially oriented with respect to the cornea when sufficient hand pressure is applied to said knife assembly.

2. The surgical instrument according to claim 1 further comprising means for indexing said knife assembly about said pivot point at predetermined incremental intervals.

3. The surgical instrument according to claim 2 wherein said means for incremental indexing comprises a plurality of indentations and at least one cooperating detent on cooperating parts of said linkage assembly and knife assembly.

4. The surgical instrument according to claim 2 further comprising a scale carried on said instrument for indicating the degree of indexing movement of said knife assembly with respect to said linkage assembly to permit predetermined pivotal movement of said knife assembly about said pivot point.

5. The surgical instrument according to claim 2 further comprising means carried by said knife assembly for varying and controlling the depth of insertion of the knife blade into the eye.

6. The surgical instrument according to claim 5 wherein said means for varying the depth of insertion of the knife blade into the eye comprises a gear rack positioned along one longitudinal edge of said knife blade, a pinion gear rotatably carried within said knife blade holder and positioned for engagement with said gear rack when said knife blade is supported in said knife blade holder, and means connected with said pinion for causing rotation thereof so as to produce axial movement of said knife blade for varying the amount of exposure of the cutting edge of said knife blade from one end of said blade holder.

7. The surgical instrument according to claim 6 further comprising a scale carried on another longitudinal edge of said knife blade to indicate relative exposure of said cutting edge.

8. The surgical instrument according to claim 2 wherein said fixation means comprises a pair of elongated arms fixed at one end thereof to each other so that the other ends thereof are movable toward and away from each other, a prong carried at said other end of said elongated arms for insertion into the globe of a human eye for immobilizing the eye when said fixation means are hand-held by a surgeon, and finger grip means on said arms.

9. A hand-held surgical instrument for performing radial ophthalmological incisions comprising fixation means for supporting said instrument on the globe of an eye and adapted to be held in one hand of a surgeon; said fixation means comprising a pair of elongated arms fixed at one end thereof to each other so that the other ends thereof are movable toward and away from each other, a prong carried at said other end of said elongated arms for insertion into the globe of a human eye for immobilizing the eye when said fixation means are hand-held by a surgeon, and finger grip means on said arms; a linkage assembly connected to said fixation means; a knife assembly connected to said linkage assembly at a pivot point for indexing movement thereabout and including a knife blade holder and a knife blade removably carried therein for forming incisions in the eye of a patient; means for indexing said knife assembly about said pivot point at predetermined incremental intervals; said linkage assembly comprising first and second "L" shaped linkage arms, each said arm having first and second legs, the distal end of said first leg of each arm being pivotally connected to one of said elongated arms of said fixation means, the distal end of the second leg of each of said "L" shaped arms being pivotally connected together defining said pivot point; and means for supporting said knife blade and said knife blade holder in said knife assembly to permit movement of said knife blade along a path, so that when said surgical instrument is in an operative position and said blade is moved along said path, said blade will penetrate in eye to form an incision radially oriented with respect to the cornea when sufficient hand pressure is applied to said knife assembly.

10. The surgical instrument according to claim 9 further comprising a shoulder carried on each arm of said fixation means, an aperture provided in each said shoulder, and rivet means adapted to extend through said apertures and through the distal end of said first leg of each arm of said linkage assembly for pivotally connecting said "L" shaped linkage arms to said arms of said fixation means.

11. The surgical instrument according to claim 9 wherein said knife assembly includes a third linkage arm pivotally connected at one end thereof to said second leg of said first and second "L" shaped linkage arms at said pivot point, said knife blade holder being carried by said third linkage arm.

12. The surgical instrument according to claim 11 wherein said third linkage arm comprises a flange, an aperture carried in said flange for connecting said third linkage arm to said second leg of said first and second "L" shaped linkage arms of said linkage assembly at said pivot point, a pair of spaced parallel walls connected to said flange and extending away from said pivot point, parallel guide slots formed in each of said walls along a curved path, and means for supporting said knife blade holder between said walls for movement toward and away from said pivot point.

13. The surgical instrument according to claim 12 wherein said means for supporting said knife blade holder between said walls comprises a pair of oppositely extending trunnions carried by said knife blade holder and positioned within said guide slots of said walls, said trunnions having flat surfaces to prevent swinging movement thereof.

14. The surgical instrument according to claim 13 further comprising a scale carried on one of said walls and a pointer carried by said knife blade holder so that said pointer will indicate the length of the incisions as said holder is moved along said slots.

15. The surgical instrument according to claim 14 wherein the guide slots on each of said walls are equidistantly positioned from the surface of the cornea when the fixation device is held in the operative position so that as said knife blade is moved along the curved path of said slots the incision formed thereby will be perpendicular to the surface of the cornea.

16. The surgical instrument according to claim 13 wherein said first, second and third linkage arms are connected by a rivet passing therethrough.

17. The surgical instrument according to claim 16 further comprising indicia carried on the head of said rivet, and a pointer carried by said knife blade assembly for alignment with said indicia to indicate the degree of indexing of said knife blade assembly about said pivot point.

18. The surgical instrument according to claim 9 wherein said means for incrementally indexing said knife blade about said pivot point comprises detent means carried on one of said linkage assembly or knife assembly, and mating indentation means carried on the other of said linkage assembly or knife assembly for positive engagement therebetween.

* * * * *